(12) United States Patent
Stoianovici et al.

(10) Patent No.: US 10,159,469 B2
(45) Date of Patent: Dec. 25, 2018

(54) COHESIVE ROBOT-ULTRASOUND PROBE FOR PROSTATE BIOPSY

(71) Applicant: THE JOHNS HOPKINS UNIVERSITY, Baltimore, MD (US)

(72) Inventors: Dan Stoianovici, Reisterstown, MD (US); Misop Han, West Friendship, MD (US); Doru Petrisor, Lutherville, MD (US); Chunwoo Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 325 days.

(21) Appl. No.: 14/391,771

(22) PCT Filed: Apr. 10, 2013

(86) PCT No.: PCT/US2013/035928
§ 371 (c)(1),
(2) Date: Oct. 10, 2014

(87) PCT Pub. No.: WO2013/155156
PCT Pub. Date: Oct. 17, 2013

(65) Prior Publication Data
US 2015/0065886 A1    Mar. 5, 2015

Related U.S. Application Data

(60) Provisional application No. 61/622,130, filed on Apr. 10, 2012.

(51) Int. Cl.
*A61B 10/02* (2006.01)
*A61B 8/12* (2006.01)
(Continued)

(52) U.S. Cl.
CPC ........ *A61B 10/0241* (2013.01); *A61B 8/0841* (2013.01); *A61B 8/12* (2013.01);
(Continued)

(58) Field of Classification Search
CPC ...... A61B 10/0241; A61B 2017/00274; A61B 2017/3413; A61B 2018/00547;
(Continued)

(56) References Cited

U.S. PATENT DOCUMENTS 5,398,690 A  *  3/1995  Batten .................. A61B 8/0833
                                                              600/439
6,102,867 A     8/2000  Dietz et al.
(Continued)

FOREIGN PATENT DOCUMENTS

WO    2004019799 A2    3/2004
WO    2006089426 A1    8/2006
WO    2007085953 A1    8/2007

OTHER PUBLICATIONS

Ho, H., et al., "Robotic prostate biopsy and its relevance to focal therapy of prostate cancer", Nature Reviews Urology, (2011) vol. 8, No. 10, pp. 579-585.
(Continued)

*Primary Examiner* — Michael Rozanski
(74) *Attorney, Agent, or Firm* — Johns Hopkins Technology Ventures (57) ABSTRACT

An embodiment in accordance with the present invention provides a device and method for a transrectal ultrasound (TRUS) guided prostate biopsy. The device includes an ultrasound wand equipped with a lateral fire ultrasound sensor. The ultrasound wand also defines a channel having an oblique path though the wand. The channel accommodates a biopsy needle, which can be pivoted as well inserted through the channel to different depths in order to perform
(Continued)

a biopsy of the prostate. The device therefore uses only three degrees-of-freedom of movement in order to obtain the biopsy samples. Additionally, the ultrasound wand can be used to generate a three-dimensional image of the prostate.

12 Claims, 6 Drawing Sheets

(51) Int. Cl.
*A61B 19/00* (2006.01)
*A61B 8/08* (2006.01)
*A61B 34/30* (2016.01)
*A61B 17/00* (2006.01)
*A61B 17/34* (2006.01)
*A61B 18/00* (2006.01)
*A61B 8/00* (2006.01)
*A61B 90/00* (2016.01)

(52) U.S. Cl.
CPC ............ *A61B 34/30* (2016.02); *A61B 8/4245* (2013.01); *A61B 2017/00274* (2013.01); *A61B 2017/3413* (2013.01); *A61B 2018/00547* (2013.01); *A61B 2090/3782* (2016.02); *F04C 2270/0421* (2013.01)

(58) Field of Classification Search
CPC ............ A61B 2090/3782; A61B 34/30; A61B 8/0841; A61B 8/12; A61B 8/4245; F04C 2270/0421

See application file for complete search history.

(56) References Cited

U.S. PATENT DOCUMENTS

| | | | |
|---|---|---|---|
| 2005/0159676 A1* | 7/2005 | Taylor | A61B 10/0266 |
| | | | 600/567 |
| 2005/0203413 A1 | 9/2005 | Fichtinger et al. | |
| 2008/0039723 A1 | 2/2008 | Suri et al. | |
| 2009/0030339 A1* | 1/2009 | Cheng | A61B 8/0833 |
| | | | 600/562 |
| 2009/0171218 A1* | 7/2009 | Nygaard | A61B 8/0833 |
| | | | 600/461 |
| 2010/0056900 A1 | 3/2010 | Whitcomb et al. | |
| 2010/0172559 A1 | 7/2010 | Kumar et al. | |
| 2012/0157841 A1* | 6/2012 | Glaenzer | A61B 8/12 |
| | | | 600/439 |

OTHER PUBLICATIONS

Shao, W., et al., "Integrating MRI and MRSI information into TRUS-guided robotic prostate biopsy", International Journal of Humanoid Robotics, (2006), vol. 3, No. 4, pp. 499-522.

Phee, L., et al., "Ultrasound guided robotic biopsy of the prostate", International Journal of Humanoid Robotics, (2006), vol. 3, No. 4, pp. 463-483.

\* cited by examiner

COHESIVE ROBOT-ULTRASOUND PROBE FOR PROSTATE BIOPSY

CROSS-REFERENCE TO RELATED APPLICATIONS

This application is a 35 U.S.C. § 371 U.S. national entry of International Application PCT/US2013/035928, having an international filing date of Apr. 10, 2013, which claims the benefit of U.S. Provisional Application No. 61/622,130, filed Apr. 10, 2012, the content of each of the aforementioned applications is herein incorporated by reference in their entirety.

FIELD OF THE INVENTION

The present invention relates generally to diagnostic screening. More particularly, the present invention relates to a device for performing a prostate biopsy.

BACKGROUND OF THE INVENTION

Prostate cancer (PCa) is the most frequently diagnosed non-skin malignancy for men in the United States. Studies have shown that it is necessary to treat 48 men to prevent one death from PCa, suggesting that significant overtreatment exists. On the other hand, in 2010 more than 32,000 men died of PCa. Surgery and radiation therapy can achieve excellent cancer control, but both surgery and radiation therapy are associated with adverse effects and an increased burden to our healthcare system. Alternative management options evolved, such as active surveillance (watchful waiting) and focal ablations. Yet these alternative management options rely heavily on biopsy. The current transrectal ultrasound-guided (TRUS) prostate biopsy, however, has significant shortcoming and high false-negative rates, largely related to targeting inaccuracies.

Many biopsy navigation devices for TRUS and 3D probes have been proposed to guide the biopsy. These biopsy navigation devices address several targeting error components but are commonly affected by prostate deformations, which are difficult to account for and to quantify. These errors may be relatively large. In fact, these errors can be larger than the radius of a "clinically significant" PCa tumor, and therefore, these errors alone can deteriorate the targeting plan.

Several technologies have been proposed to improve prostate biopsy. These technologies include 3D sonography, probe position tracking, image-fusion, and robotics. Using 3D ultrasound not only provides images of the prostate region, but also helps the physician's mnemonic perception of the anatomy and potentially improves his/her ability to sample the prostate more uniformly. For 3D ultrasound, multi-plane images are acquired by sensor arrays or using a mechanism that moves a sensor within the probe. Sensor array probes produce faster 3D acquisition but image quality and resolution tend to be lower because of space constraints, limiting the ability to guide the biopsy, because anatomic landmarks are more difficult to distinguish. Internal motion scanning probes preserve 2D image quality but have longer acquisition times, making it difficult to guide the intervention in real-time.

Several methods of tracking (continuously measuring) the location of TRUS probes have been proposed. Probe location is first used to render in 3D the prostate volume scanned by the images and then use these images to provide navigation to guide the biopsy. Optical and electromagnetic position trackers have been adapted to measure the location of the TRUS probe.

However, these systems generally require the use of a transperineal biopsy path or cause deflections of the prostate. The transperineal path is rarely used for biopsy because it causes more discomfort for the patients. This approach uses numerous biopsy cores, up to 100, and is performed in the operating room under anesthesia. However, to date this remains the most comprehensive way of biopsy because it gives more control on biopsy localization. But, for most of the biopsy patient population-at-large, the transperineal biopsy is logistically and economically unfeasible. Thus, there is a critical need for more accurate devices to perform the common TRUS-guided transrectal biopsy.

Current freehand TRUS-guided prostate biopsy inherently moves and deforms the gland (displacement+deformation=deflection). Typically, the TRUS probe causes variable deflection of the gland while imaging. The resulting images are distorted, and the volume is skewed and not entirely reliable if rendered in 3D. Deflections are very difficult to quantify and correct.

Figure 1A:
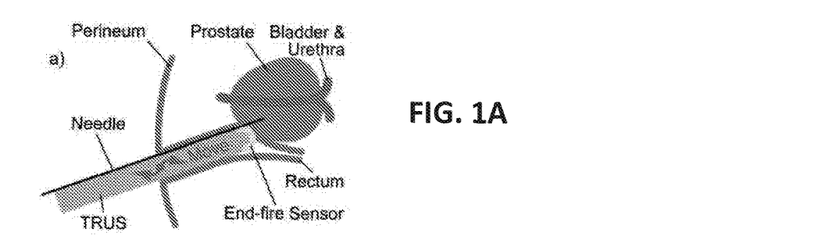
FIGS. 1A-1E illustrate common TRUS imaging planes and biopsy paths.

Several common TRUS imaging planes and biopsy paths are included in FIGS. 1A-1E. These schematics aim to explain the types of prostate deflections. FIG. 1A shows the current standard of care. A 2D TRUS probe typically uses an end-fire sector ultrasonic sensor. A needle-guide adapter is attached parallel to the probe to guide the needle within the plane of the sensor, so that needle insertion can be seen in ultrasound. The probe is freehanded by the physician, who first moves the probe to understand the 3D anatomy, and second aligns the probe for each biopsy based on a mnemonic plan. Alignment is held with one hand while the other inserts the needle and triggers the biopsy. This is a very common but difficult task with subjective planning, navigation, and quality control. Among the problems is that prostate deflections are inexorable because the sensor must keep in contact with the rectum for the sonic waves to propagate. Pressing against the rectum deflects the prostate, more or less depending on the ultrasound coupling gel and physician's handling abilities. The schematic shows a simple indentation, but in reality deflections may be complex. While freehanded, it is nearly impossible to maintain the state of deflection while imaging and taking the biopsy.

With 3D and/or tracked TRUS the probe is still freehanded. Navigation and/or 3D are very helpful for the physician, but prostate deflections and derived skewed image problems remain. This is also the case for TRUS-MRI fusion based on freehanded TRUS, deflections further deteriorating fusion accuracy.

For the accuracy of image-guided biopsy targeting it is essential that the scanned volumetric images are geometrically accurate, and at the time when the biopsy is targeted the prostate has not geometrically changed from its initially imaged state, based on which the biopsy plan was made. If a certain level of compression is necessary for sound wave propagation, the same level must be maintained throughout. Several systems achieve this requirement for imaging and/or transperineal biopsy and brachytherapy.

Figure 1B:
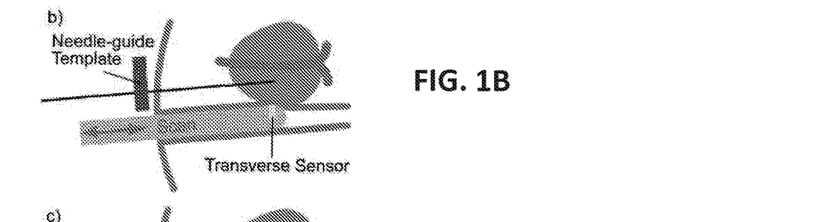

Brachytherapy stabilizers were the first devices to support the probe. Here, probes use primarily a transverse ultrasound sensor, as illustrated in FIG. 1B. Images are scanned by stepping the probe in and out. As illustrated, this may also induce deflections at the end of the probe, but these should be somewhat repeatable at the same depth. The needle is passed transperineally through a needle-guide template of parallel holes. Transrectal needle access is unfeasible.

Figure 1C:
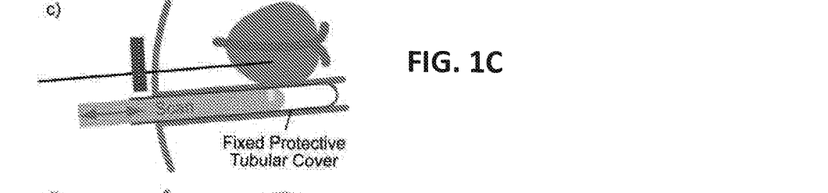

An essential advance was the addition of a fixed protective tubular cover, illustrated in FIG. 1C. The stepper now moves the probe within the cover so that the state of prostate deflection is preserved. This approach was first used by the TargetScan system and scan motion was motorized. The BioXbot adds robotic motion for the needle as well. Both work on the transperineal path.

Figure 1D:
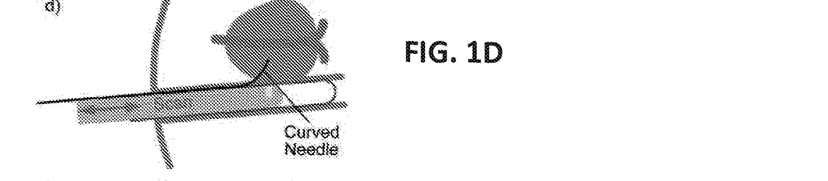

TargetScan has also made a transrectal needle-guide adapter, but the only way to target the prostate was to bend the needle, as illustrated in FIG. 1D. However, that was problematic because core biopsy needles have internally moving parts which may jam if bent. But perhaps more difficult to account are targeting errors. When a needle is curved the amount of resistance encountered at the needle point contributes to its curvature making targeting uncertain when passing the heterogeneous tissues.

Figure 1E:
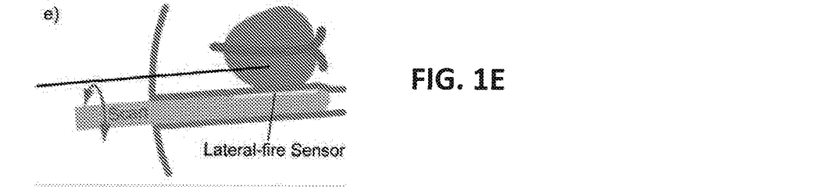

Recently, an alternative to the protective tubular cover was implemented on the University of Western Ontario robot by using a lateral-fire probe and with a purely rotary scan, as shown in FIG. 1E. Prostate deflections are preserved because the probe is round and well lubricated by the ultrasound coupling gel. This approach can be used for TRUS-guided prostatectomy. Most recently this approach was also used in a robot for prostatectomy navigation and elastography at the University of British Columbia, Vancouver, Canada.

Figure 1F:
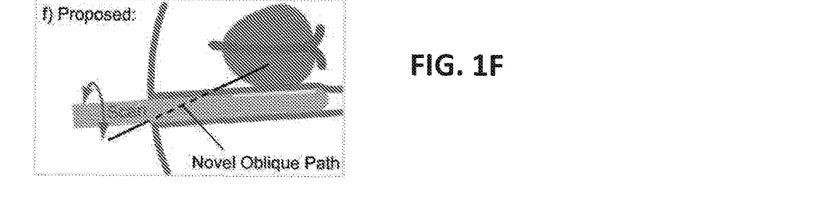
FIG. 1F illustrates an imaging plane and biopsy path according to an embodiment of the present invention.

An apparent problem with the lateral-fire rotary scan approach is that it can't be used for transrectal biopsy. However, it was observed that an oblique trajectory of the needle relative to the probe allows a straight needle to target the prostate, as shown in FIG. 1F. For this approach however, the needle must cross the shaft of the probe, which is not possible with current probes. There appears to be only one probe that presents a lateral slot on the side of the shaft, the BK Medical 8818. However, this probe does not have a lateral-fire sensor. Moreover, the needle-guide is locked to the probe thus inducing deformations when aligning for biopsy. Another possible approach is to pass the needle oblique but on the probe side. However, this is problematic because the needle may injure the anus and cause significant discomfort, and because the needle will lie outside the ultrasound plane making it difficult to monitor.

It would therefore be advantageous to provide a new TRUS probe for imaging the prostate with minimal deflection and an oblique path for the needle to follow for biopsy, thus allowing for an accurate transrectal biopsy path.

SUMMARY OF THE INVENTION

The foregoing needs are met, to a great extent, by the present invention, wherein in one aspect a system for performing biopsy of a prostate includes an ultrasound wand. The ultrasound wand has a probe having a housing and a proximal end and a distal end, the housing further defining a channel, and the channel takes an oblique path though the probe. The probe includes a lateral fire sensor positioned within the housing of the probe. A handle is operatively coupled to the probe, such that the probe rotates about a longitudinal axis of the handle. Additionally, a biopsy needle can be configured for insertion through the channel, such that the prostate can be biopsied.

In accordance with another aspect of the present invention, the handle includes a first motor to rotate the probe about the longitudinal axis of the handle. The probe can also include a needle guide pivot disposed adjacent to the channel, which provides the biopsy needle with a first degree-of-freedom of movement. A second motor is operatively coupled to the needle guide pivot to pivot the biopsy needle within the channel. A spacer can also be included, such that the depth of the needle is adjustable thus providing a second degree-of-freedom to the biopsy needle.

In accordance with yet another aspect of the present invention, an ultrasound wand includes a probe having a housing and a proximal end and a distal end, the housing further defining a channel configured to accept a biopsy needle, wherein the channel is defined by the housing to have an oblique path though the probe. The probe also includes a lateral fire sensor positioned within the housing of the probe. A handle is operatively coupled to the probe, such that the probe rotates about a longitudinal axis of the handle.

In accordance with still another aspect of the present invention, the handle includes a first motor to rotate the probe about the longitudinal axis of the handle. The probe can further include a needle guide disposed adjacent to the channel. The needle guide provides the biopsy needle with a first degree-of-freedom of movement, and a second motor is operatively coupled to the needle guide to pivot the biopsy needle within the channel. A spacer can also be included, such that the depth of the needle is adjustable thus providing a second degree-of freedom to the biopsy needle.

In accordance with yet another aspect of the present invention, a method for performing a biopsy of a prostate includes imaging the prostate using an ultrasound wand having a lateral fire sensor. The method also includes inserting a biopsy needle through a channel defined by a probe of the ultrasound wand, wherein the channel defines an oblique path though the probe and pivoting the biopsy needle within the channel in order to direct the biopsy needle to a predetermined point on the prostate. The method further includes adjusting the depth of the biopsy needle within the channel in order to direct the biopsy needle to the predetermined point on the prostate, and taking the biopsy of the prostate at the predetermined point.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 4A and 4B illustrate a CAD simulation of prostate targeting.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a device and method for a transrectal ultrasound (TRUS) guided prostate biopsy. The device includes an ultrasound wand equipped with a lateral fire ultrasound sensor that fits the entire prostate in parasagittal views. A purely rotary and controlled motion about the probe axis is used to scan the entire prostate. The ultrasound wand also defines a channel having an oblique path though the wand. The channel accommodates a biopsy needle, which can be pivoted relative to the probe, as well as inserted through the channel to different depths in order to perform a biopsy of the prostate. The device therefore uses only three degrees-of-freedom (DoF) of movement in order to obtain the biopsy samples. The wand can also be used in conjunction with robotic control. Additionally, the ultrasound wand can be used to generate a three-dimensional image of the prostate.

Figure 2A:
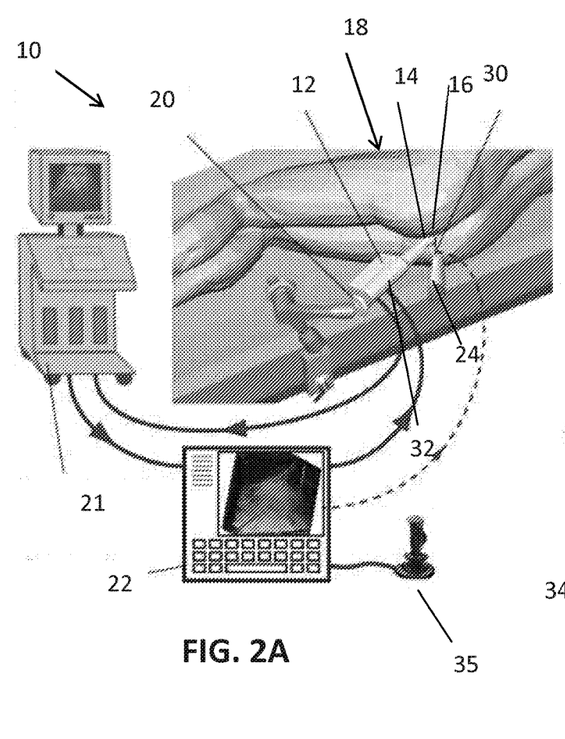
FIGS. 2A and 2B illustrate a schematic diagram of a system for performing a prostate biopsy, according to an embodiment of the invention.
Figure 2B:
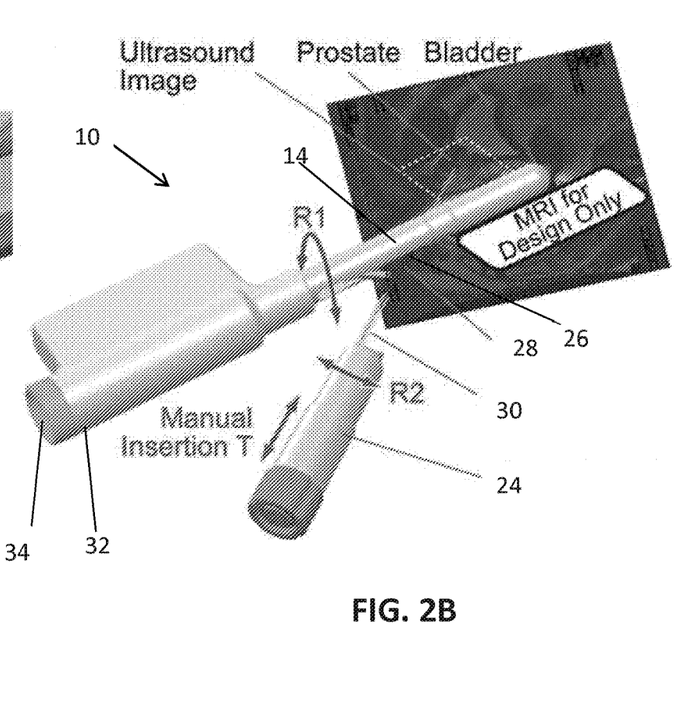

FIGS. 2A and 2B illustrate, a schematic of the proposed biopsy system and setup. As shown in FIGS. 2A and 2B, a system 10 includes a robotic-TRUS (R-TRUS) wand 12 having a probe 14 that can be inserted into a rectum 16 of a patient 18. The R-TRUS wand 12 is held in place by an arm 20. The R-TRUS wand 12 is also connected to a standard two-dimensional ultrasound 21 and controller 22. Further, as illustrated in FIGS. 2A and 2B, a biopsy needle 24 can be inserted through a channel 26 defined by the probe 14. The biopsy needle 24 is inserted obliquely relative to the probe 14 of the R-TRUS wand 12. The channel 26 can further include a needle guide 28 for limiting the motion of the biopsy needle 24. A needle spacer 30 can be used for controlling the depth to which the biopsy needle 24 is inserted.

The R-TRUS wand 12 can also include a handle 32 as illustrated in FIGS. 2A and 2B. The handle 32 contains the robotics for controlling the R-TRUS wand 12 and needle guide 28. These robotics will be discussed in further detail below, but overall the R-TRUS wand 12 has 3 degrees-of-freedom. Two degrees-of-freedom are implemented on the probe and a third, remote degree of freedom is implemented on a small needle-spacer that attaches to the needle. The needle can take the form of a standard 18 Ga biopsy needle. Alternately, the needle can take the form of any other needle or biopsy device known to or conceivable by one of skill in the art.

By way of example, the procedure can proceed as follows, however, the procedure discussed below is not to be considered limited to only the following methodology. After confirming that appropriate antibiotics and fleet enema are given to minimize infection, the patient is placed in a lateral decubitus position on the examination table in the urology clinic. Soft blocks around lower extremities are used to maintain the patient's position and local anesthesia is administered with a periprostatic Lidocaine block to minimize patient discomfort and motion. The probe 14 of the R-TRUS wand 12, detached from the support arm 20 is inserted manually. The probe is adjusted, such that the lateral-fire ultrasound shows the entire sagittal view of the prostate shown in FIG. 2B, using an image from an MRI scan. The R-TRUS wand 12 can also include a quick-connect coupler 34 to attach the wand 12 to the support arm 20. The physician uses a joystick 35 to rotate the probe 14 about its axis confirming that the entire prostate is visible, side-to-side. An automated rotary scan is performed to uniformly sweep the entire gland and record image-position pairs. Pixels of the 2D image slices are mapped in 3D using volume rendering. This 3D mapping can be executed immediately.

The biopsy plan is overlaid as described further, herein. The R-TRUS wand 12 automatically rotates and angles its oblique needle-guide 28 to point to the planned locations of biopsy, one after another. Automatically, the active spacer 30 of the needle adjusts its length to match the depth of the target. Real-time B-mode images are presented to the physician. The planned needle trajectory and target may be superimposed as needed. If necessary, the physician can choose to correct the alignment using the joystick. Manually, he/she then inserts the needle, fires the biopsy, collects, and labels the sample. The oblique needle-guide 28 is in the central lane of the sensor, enabling the physician to monitor the insertion. Ultrasound images are also recorded to document the actual biopsy locations. The actual locations are calculated in 3D based on the images and the corresponding angles of the probe. The biopsy map with matching sample labeling accompanies the histopathologic biopsy report.

The body of the R-TRUS wand 12 is fixed with a support arm 20 through a quick-connect coupler 34, as illustrated in FIG. 2A. A 7-DoA (degrees of adjustment) passive arm can be used with a coupler, such as a threaded coupler, a frictional coupler, or a magnetic coupler, or any other suitable form of coupler. Disconnecting the wand 12 from the arm 20 facilitates placement of probe 14 in the rectum 16. It can also make it easy to remove the probe 14 for cleaning, and enhance safety as a quick disconnect.

Figure 3:
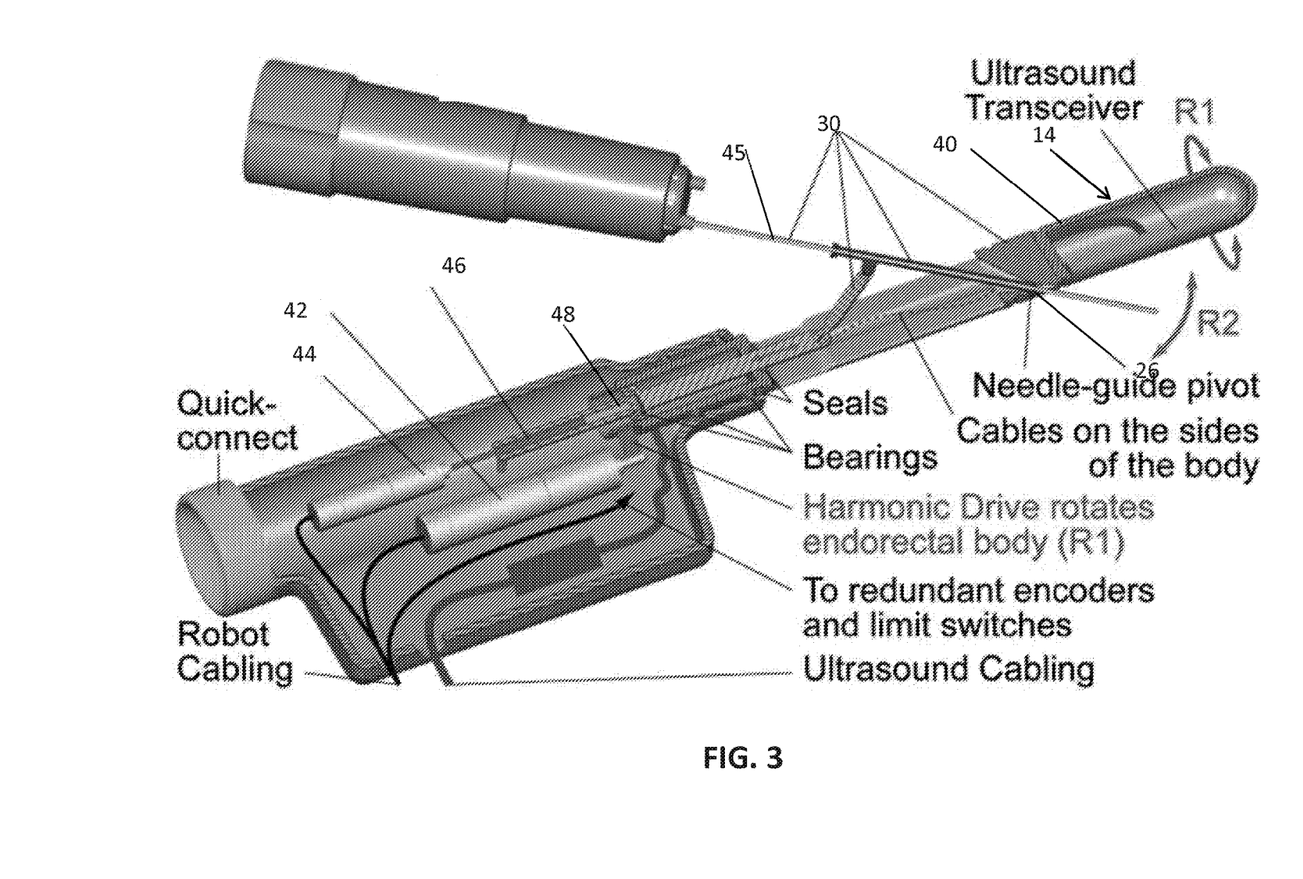
FIG. 3 illustrates a sectional view of an ultrasound wand and robotics unit according to an aspect of the present invention.

FIG. 3 illustrates a sectional view of an ultrasound wand and robotics unit according to an aspect of the present invention. The endorectal shaft 40 of the probe 14 spins about an axis (R1) controlled by the R1 motor 42 through a transmission, preferably a harmonic drive. The R2 motor 44 pushes a rod 46 through a ball-screw 48, which acts upon the 3-bar mechanism of the needle-guide, adjusting the angle of the guide, R2. A central through shaft opening 26 is made to accommodate the needle-guide components 28. The ultrasound transceiver is hermetically closed at the end of the probe. Its cables are passed on the sides of the shaft into the body of the probe, and mounted loose to allow the shaft to rotate. For this, R1 is limited to approximately ±90°. Two bearings support the shaft for smooth motion, and another on the rod decouples the R1 and R2. The shaft and rod are round so O-rings are used to seal the body hermetically.

Figure 4A:
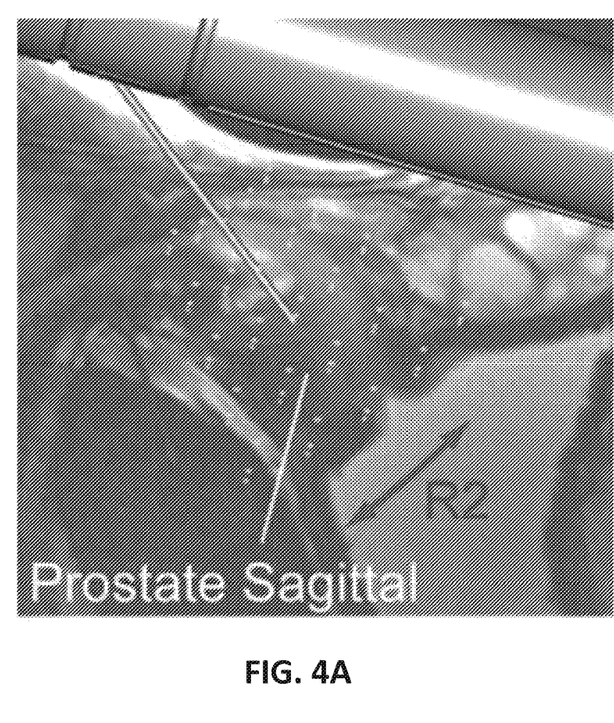
FIG. 4A is a sagittal view and FIG. 4B is a coronal view.
Figure 4B:
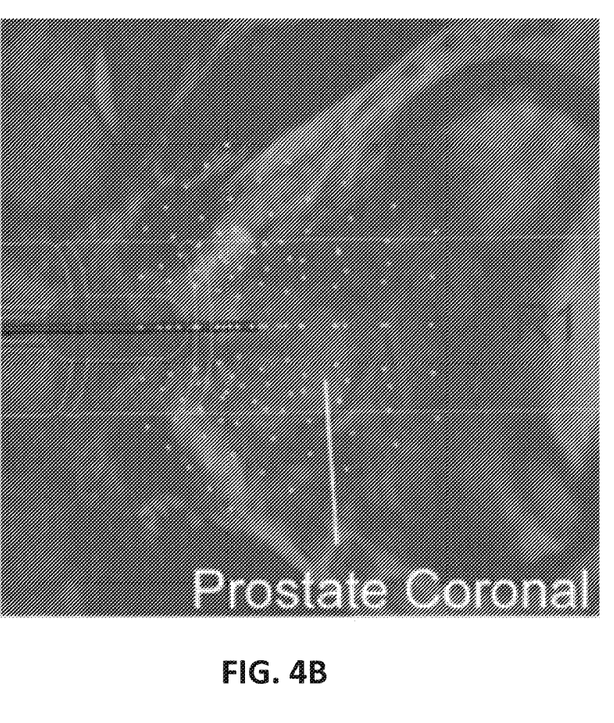

For example, the CAD scene built with a sagittal pelvic MRI illustrated in FIG. 3 shows that the needle 24 can occupying the space taken by the ultrasound sensor and target the prostate without injuring the anus. FIGS. 4A and 4B show a CAD simulation of prostate targeting. FIG. 4A is a sagittal view and FIG. 4B is a coronal view. As shown, the needlepoint density plot overlaps the prostate in the two orthogonal views showing that the 3-DoF are properly selected and dimensioned to target the gland.

Further, as illustrated in FIG. 3, a spacer 30 with adjustable length is placed over a shaft 45 of the needle 24. The length of this spacer 30 is adjusted automatically under image-guided control. When the needle 24 and spacer 30 are fully inserted into the needle-guide 26 and fired, the center of the biopsy core matches the depth of the biopsy target. Any biopsy needle or biopsy device known to or conceivable to one of skill in the art can be used. For example, an 18 Ga biopsy needle is common for the prostate, but any suitable biopsy needle can be used. The spacer 30 can be connected with a flexible cable to the robot controller, as illustrated in FIGS. 3, 4A, and 4B.

Figure 5:
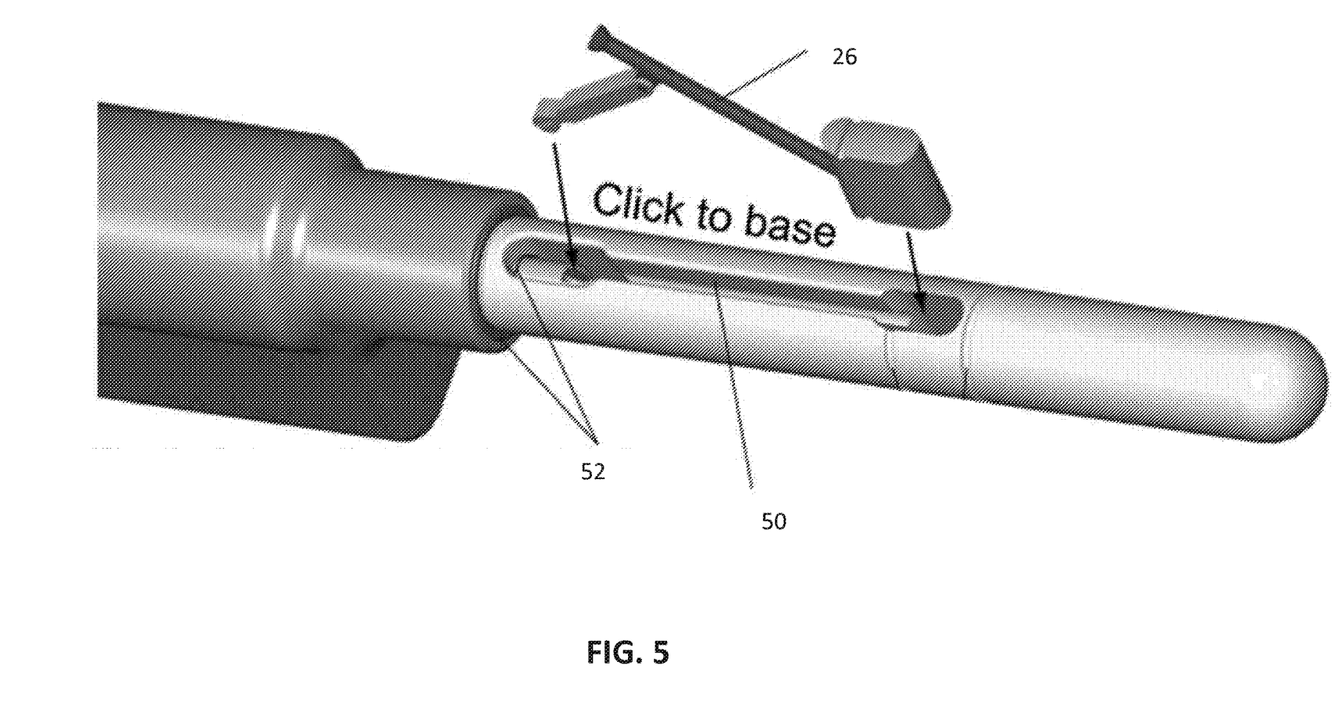
FIG. 5 is a perspective view of the probe of an ultrasound wand according to an aspect of the present invention.

The present invention also includes cleaning and sterilization features, as illustrated in FIG. 5. The needle-guide 26 includes parts that come in contact with the needle that should be sterile. To enable cleaning, an opening 50 extends through the shaft 40 and O-rings 52 seal the base. The sterile components of the needle guide 26 clip easily to the probe shaft 40. The sterile components of the needle guide 26 are only three simple parts that could be re-sterilized or made disposable together with the needle 24. These components can be manufactured separately or together with the biopsy needle 24.

A PC based robot controller for the R-TRUS wand can use an onboard processor motion control card. Software developments can be made in Visual C++(Microsoft Corp, Redmond, Wash.), or any other suitable programming language. A special emergency, watchdog, and relays hardware board is included to mitigate control software malfunctions. The watchdog monitors several safety functions of the robot and disables its power, should a critical situation occur. A series of principles for medical robot safety can also be included. The motors of the robot use redundant position sensors. Among other safety checks, the watchdog verifies that the outputs of the sensors are in agreement. Having reliable sensors, in turn, enables the watchdog to reliably trace following-errors for all axes. The motors are calculated and chosen so that they are not overpowered, limiting their potential force/torque in case of malfunction.

Axis level motion control can use libraries (MCI) of the motion control card. Direct and inverse kinematics of the robot are calculated based on kinematic parameters from the design. These map the robot to joint coordinates. In addition, robot-to-image registration is also required to control the robot based on the images. Registration is typically required for every intervention. For the R-TRUS wand however, the registration is maintained because of the cohesive structure. A calibration/registration procedure is performed by imaging a geometric calibration rig with the R-TRUS wand in a water tank. The mapping of the image to the robot spaces can then be calculated by comparing the 3D imaged geometry of the rig with its known geometric shape, as is known to those of skill in the art.

Image processing, visualization, robotic navigation, and biopsy planning use custom Visual C++ modules in the Amira Visualization platform (Visage Imaging Inc, San Diego, Calif.). This is a powerful image processing and visualization platform which offers open customization. Images are acquired from the standard 2D ultrasound machine with an acquisition card. Concurrently, the orientation of the image frames are available from the robot. During the rotary scan, these image-orientation pairs are saved in DICOM format including the pixel spacing (scaling), image position, and image orientation standard tags, in a volumetric DICOM form. An R-TRUS probe enables a standard 2D ultrasound to acquire 3D images. Pixels of the 2D images are mapped in 3D using volume rendering. Compared to prostate segmentation, which takes time, volume rendering can be displayed immediately. FIGS. 6A-6E illustrate a rotary slice and rendered prostate of a CIRS 053 (Norfolk, Va.) prostate mockup. Once images of the prostate are shown, biopsy locations can readily be selected by the urologist in the original B-mode parasagittal slices, re-sliced transverse slices, or other display ways as needed.

Figure 6A:
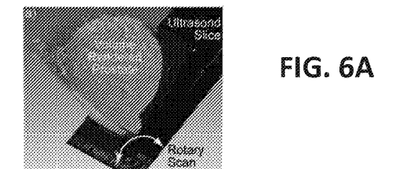
FIGS. 6A-6E illustrate a rotary slice and rendered prostate of a prostate mockup.
Figure 6B:
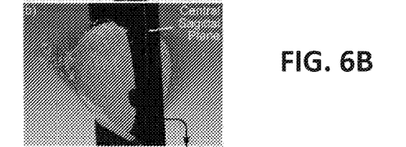
Figure 6C:
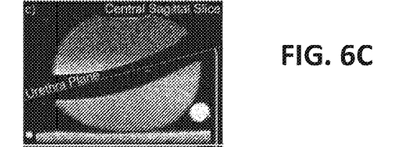
Figure 6D:
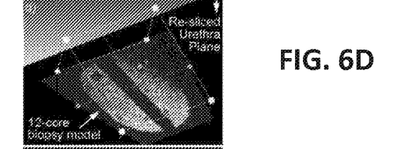
Figure 6E:
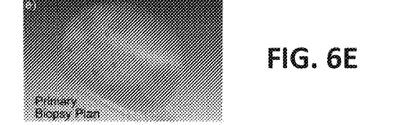

Software to implement a new way of defining the biopsy plan quickly and consistently is also included. Defining the plan involves the following 3 steps, illustrated in FIGS. 6B-6D: 1) after the scan, the central sagittal slice through the prostate is selected, as illustrated in FIG. 6B. This is one of the original B-mode rotary slices; 2) in this slice illustrated in FIG. 6C the physician outlines the general direction of the urethra, thus defining the urethra plane normal and through this line. The software then re-slices the rendered volume with the urethra plane as shown in FIG. 6D; 3) in this para-coronal slice through the urethra, the urologist places a preformatted template which already has the classic distribution of the 12-cores. This can be quickly dragged, rotated, and scaled to match the gland, by grabbing the white and green controls shown in FIG. 6D. The plan may be shown in B-mode, re-sliced views, volumetrically, shown in FIG. 6E, or any combination. It may also be adjusted by the physician as needed by editing locations independently or adjusting step 3 above.

Repeat treatment of patients with this device would be more effective because a repeat treatment could take advantage of the documented biopsy map produced. To register the old to the current images, a segmentation of the previous prostate is performed ahead of time. At the time of the intervention, this segmented prostate is aligned to the volume rendered gland. This allows registering the old biopsy sites to the new images. The physician can then decide the best approach for the new biopsy plan, either to retarget a known location of cancer in case of an active surveillance patient, or choose other locations in case of a negative previous biopsy.

While this system has been described for use in prostate biopsy, it need not be limited to this application and could be used for different imaging and biopsy procedures known to one of skill in the art. The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for performing biopsy of a prostate comprising:
   an ultrasound wand comprising:
      a probe having a housing and a proximal end and a distal end, the housing further defining a straight channel, and the straight channel takes an oblique path through the probe, wherein the straight channel comprises a first opening on a first side of the probe and a second opening on a second side of the probe, wherein the oblique path of the straight channel extends between the first opening and the second opening, and wherein the oblique path is oblique relative to a longitudinal axis of the probe;

a needle guide disposed oblique to the probe and adjacent to the straight channel;

a lateral fire sensor positioned within the housing of the probe;

a handle operatively coupled to the probe, such that the probe rotates about a longitudinal axis of the handle, wherein the handle includes a first motor to rotate the probe about the longitudinal axis of the handle;

a straight biopsy needle configured for insertion obliquely through the straight channel and through the needle guide, such that the prostate can be biopsied; and, a second motor operatively coupled to the needle guide to pivot the biopsy needle within the straight channel.

2. The system of claim 1 wherein the needle guide provides the biopsy needle with a first degree-of-freedom of movement.

3. The system of claim 1 further comprising a spacer to limit insertion depth of the needle.

4. An ultrasound wand comprising:

a probe having a housing and a proximal end and a distal end, the housing further defining a straight channel configured to accept a straight biopsy needle, wherein the straight channel is defined by the housing to have an oblique path through the probe, wherein the straight channel comprises a first opening on a first side of the probe and a second opening on a second side of the probe, wherein the oblique path of the straight channel extends between the first opening and the second opening, and wherein the oblique path is oblique relative to a longitudinal axis of the probe;

a needle guide disposed oblique to the probe adjacent to the straight channel;

a lateral fire sensor positioned within the housing of the probe;

a handle operatively coupled to the probe, such that the probe rotates about a longitudinal axis of the handle, wherein the handle includes a first motor to rotate the probe about the longitudinal axis of the handle; and a second motor operatively coupled to the needle guide to pivot the straight biopsy needle within the straight channel.

5. The ultrasound wand of claim 4 wherein the needle guide provides the biopsy needle with a first degree-of-freedom of movement.

6. The ultrasound wand of claim 4 further comprising a spacer to limit insertion depth of the needle.

7. A method for performing a biopsy with two degree-of-freedom targeting of a prostate comprising:

imaging the prostate using an ultrasound wand having a lateral fire sensor;

inserting a straight biopsy needle through a straight channel defined by a probe of the ultrasound wand, wherein the straight channel defines an oblique path through the probe, wherein a first motor is configured to rotate the probe about a longitudinal axis of a handle operatively coupled to the probe, wherein the straight channel comprises a first opening on a first side of the probe and a second opening on a second side of the probe, wherein the oblique path of the straight channel extends between the first opening and the second opening, and wherein the oblique path is oblique relative to a longitudinal axis of the probe;

pivoting the straight biopsy needle within the straight channel in order to direct the biopsy needle to a predetermined point on the prostate using a second motor;

adjusting the depth of the straight biopsy needle within the straight channel in order to direct the straight biopsy needle to the predetermined point on the prostate; and taking the biopsy of the prostate at the predetermined point.

8. The method of claim 7 further comprising using robotic control.

9. The method of claim 7 further comprising angulating a needle guide within the ultrasound wand.

10. The method of claim 9 further comprising using a degree-of-freedom taking the form of manipulating the needle guide.

11. The method of claim 7 further comprising using a cohesive ultrasound wand having first and second degrees-of-freedom of movement of the needle incorporated into the ultrasound wand.

12. The method of claim 7 further comprising generating a three-dimensional scan.

* * * * *